(12) United States Patent
Kert

(10) Patent No.: US 7,100,615 B1
(45) Date of Patent: Sep. 5, 2006

(54) LOW LEVEL LASER THERAPY SYSTEM

(75) Inventor: Jimmie Kert, Copenhagen (DK)

(73) Assignee: CMS-Dental Aps, Copenhagen (DK)

( * ) Notice: Subject to any disclaimer, the term of this patent is extended or adjusted under 35 U.S.C. 154(b) by 0 days.

(21) Appl. No.: 10/305,223

(22) Filed: Nov. 25, 2002

(51) Int. Cl.
*A61B 19/00* (2006.01)
*A61B 18/20* (2006.01)
*A61N 5/067* (2006.01)

(52) U.S. Cl. .......................... 128/898; 607/88; 607/89; 606/9; 602/2

(58) Field of Classification Search .................... 606/2, 606/8–11; 607/88–91; 128/898; 604/304, 604/308; 602/2
See application file for complete search history.

(56) References Cited

U.S. PATENT DOCUMENTS

| | | | | |
|---|---|---|---|---|
| 4,915,108 A | * | 4/1990 | Sun | 607/96 |
| 5,272,716 A | * | 12/1993 | Soltz et al. | 372/109 |
| 5,358,503 A | * | 10/1994 | Bertwell et al. | 606/27 |
| 5,464,436 A | * | 11/1995 | Smith | 607/89 |
| 5,616,140 A | * | 4/1997 | Prescott | 606/10 |
| 5,913,883 A | * | 6/1999 | Alexander et al. | 607/88 |
| 6,063,108 A | | 5/2000 | Salansky et al. | 607/89 |
| 6,084,242 A | | 7/2000 | Brown | 250/504 |
| 6,096,066 A | * | 8/2000 | Chen et al. | 607/88 |
| 6,267,780 B1 | | 7/2001 | Streeter | 607/89 |
| 6,290,713 B1 | * | 9/2001 | Russell | 607/88 |
| 6,312,451 B1 | | 11/2001 | Streeter | 607/89 |
| 6,443,883 B1 | * | 9/2002 | Ostrow et al. | 600/14 |
| 6,443,978 B1 | * | 9/2002 | Zharov | 607/91 |
| 6,510,346 B1 | * | 1/2003 | Gordon | 607/100 |
| 6,723,090 B1 | * | 4/2004 | Altshuler et al. | 606/9 |
| 2006/0009823 A1 | * | 1/2006 | Richardson et al. | 607/89 |

OTHER PUBLICATIONS

"It's only Natural, Miracle Healing with Photons" Chapter VII By Dr. Gerard Poesnecker, Sep. 9, 2002.

* cited by examiner

*Primary Examiner*—A. Farah
(74) *Attorney, Agent, or Firm*—K. David Crockett, Esq.; Marc J. Frechette, Esq.; Crockett & Crockett

(57) ABSTRACT

A low level laser therapy (LLLT) system. The laser therapy apparatus comprises a laser head and a detachable battery section. When the laser head is mounted to the battery section the apparatus assumes the shape of a penlight or flashlight and can be used as a handheld laser therapy apparatus. The detached laser heads can be placed and held in apertures of a bandage that is applied to a joint of a patient to be treated for use of the apparatus as a patient worn device.

1 Claim, 5 Drawing Sheets

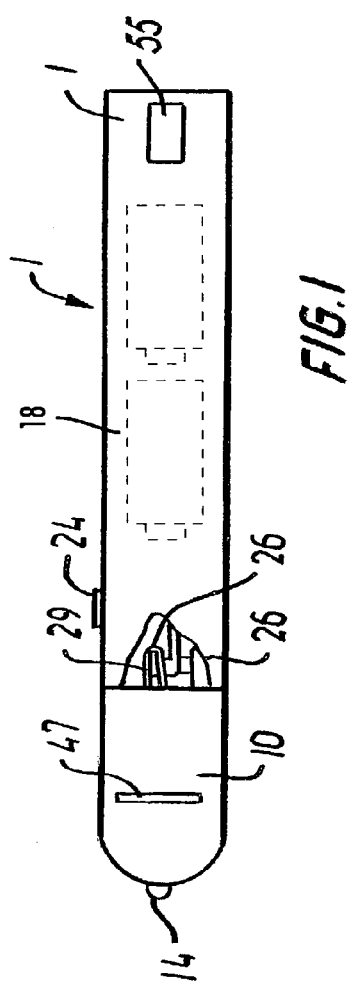
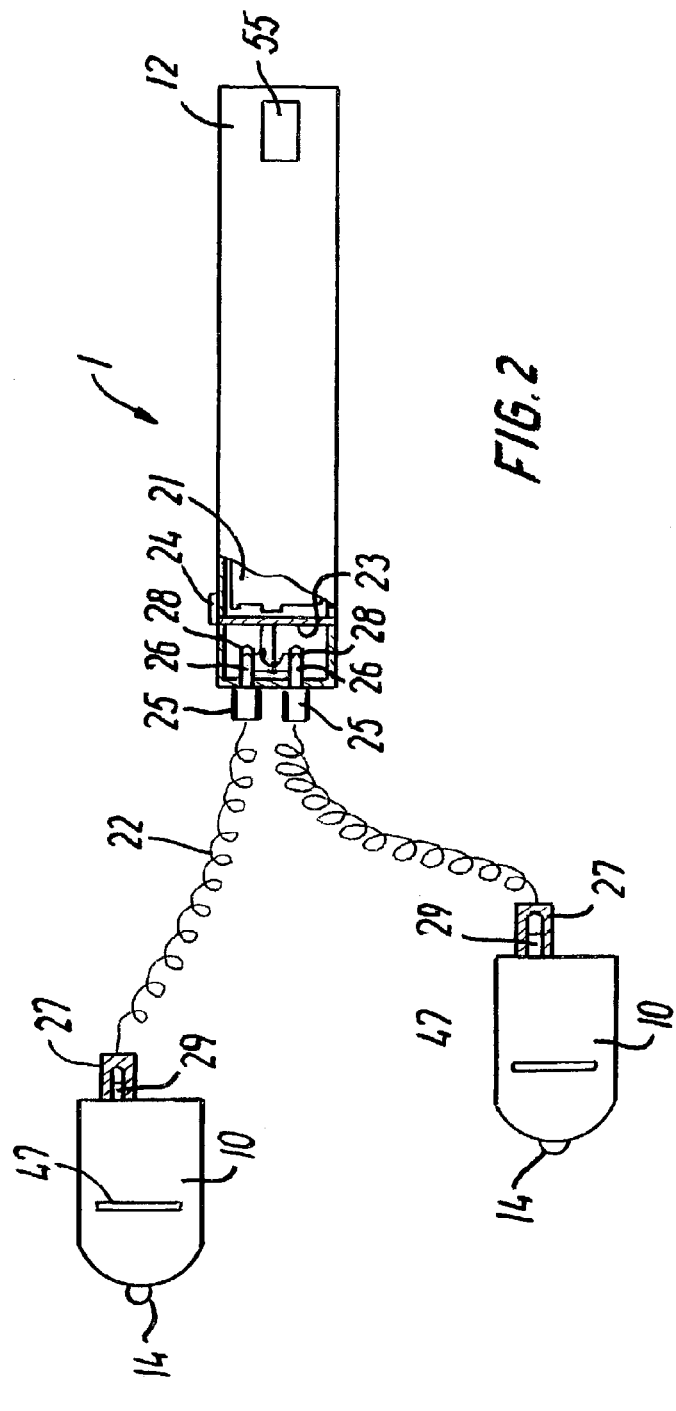
FIG.1
FIG.2

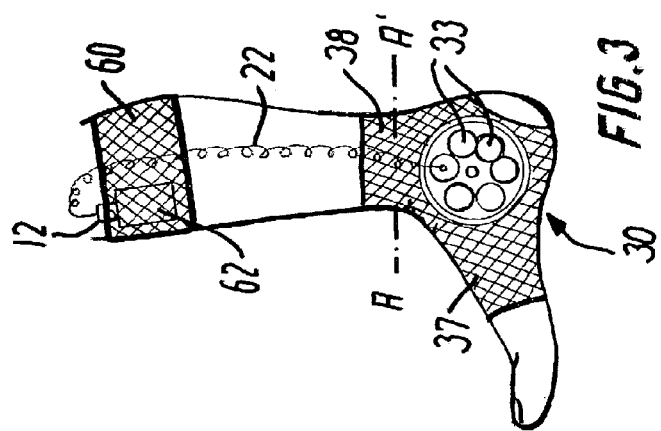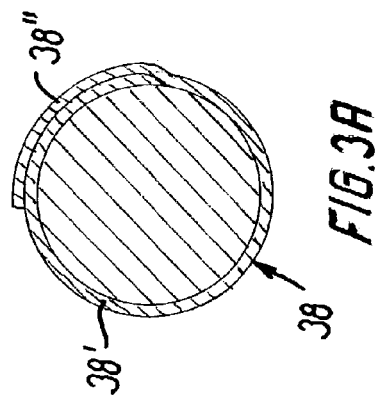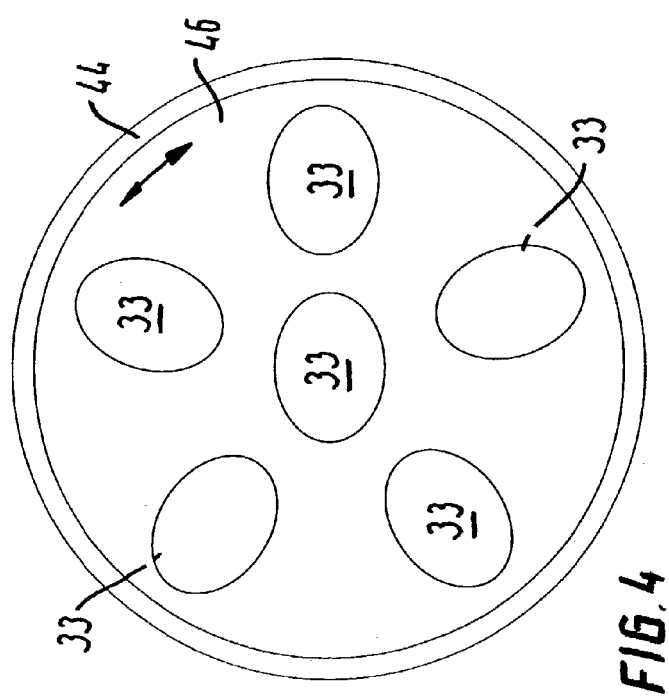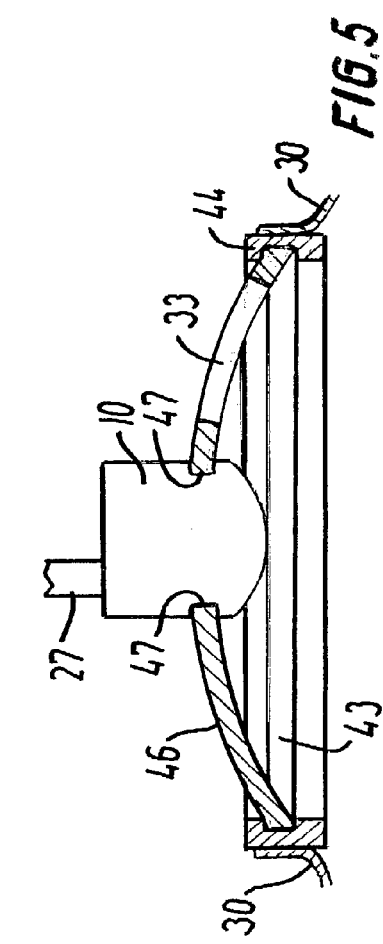

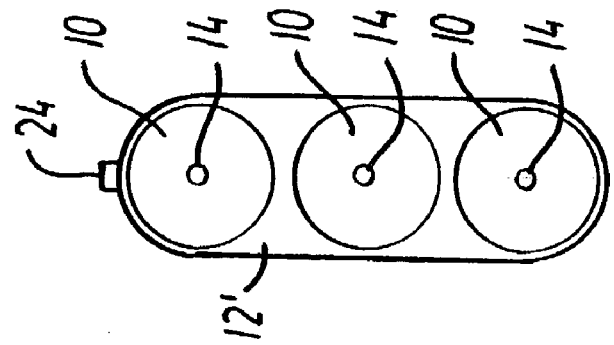
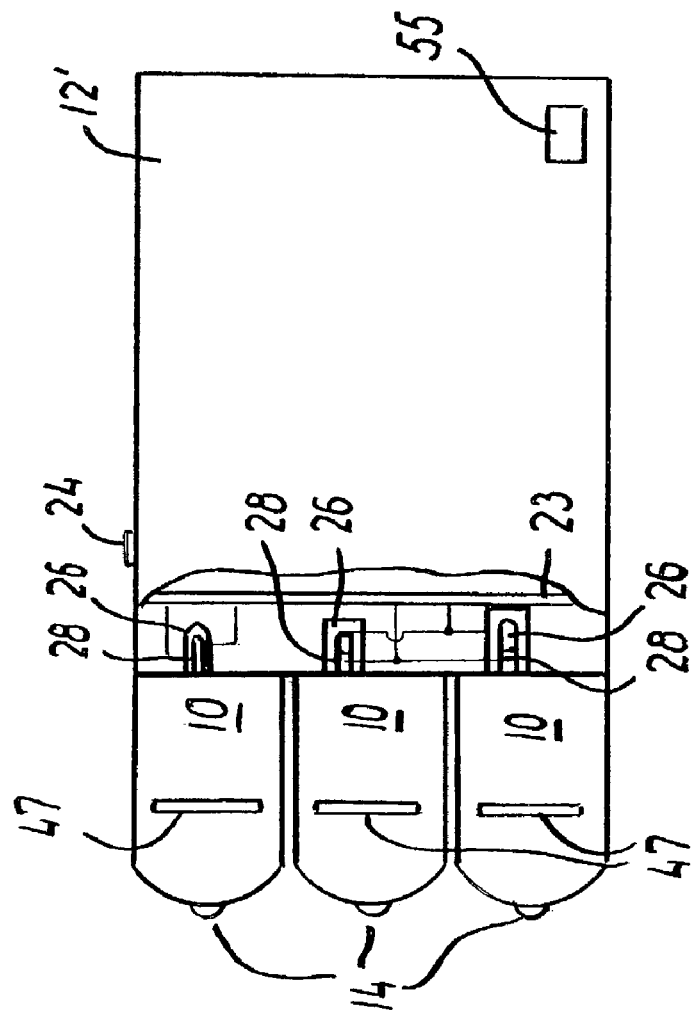

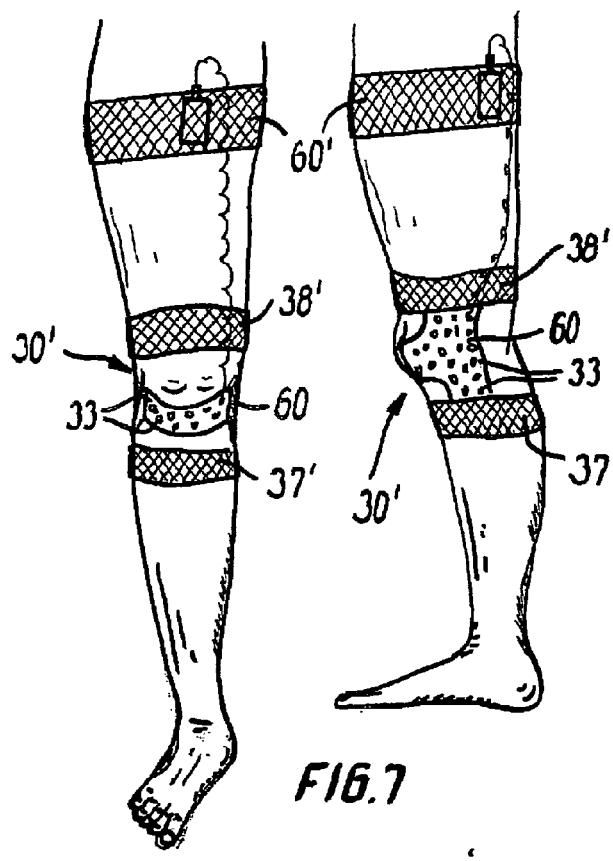
FIG. 7
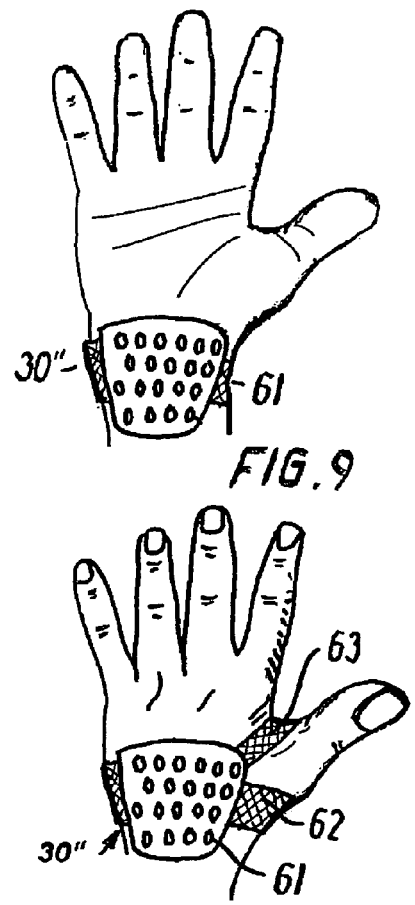
FIG. 9
FIG. 8
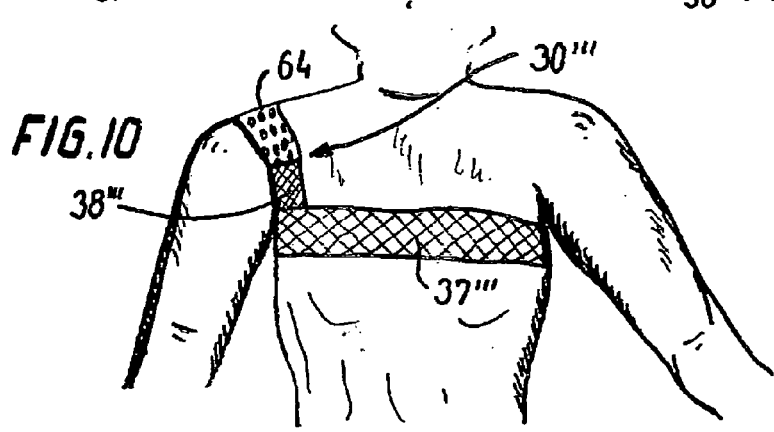
FIG. 10

LOW LEVEL LASER THERAPY SYSTEM

FIELD OF THE INVENTIONS

The inventions described below relate to a laser therapy apparatus and system, preferably used for Low Level laser Therapy (LLLT).

BACKGROUND OF THE INVENTIONS

LLLT is used to treat various injuries, including, but not limited to, inflammatory sport injuries such as epicodylitis lateralis (tennis elbow), ligament injuries, tendonitis, etc., and chronic ailments such as carpal tunnel syndrome and arthritic pain. These therapies can advantageously be applied to the human and to the animal body. The key to success with LLT is to apply the laser locally at the right spot, and at the proper dosage. The LLLT should therefore only be administered by an experienced physician, after a thorough examination.

U.S. Pat. No. 6,312,451 discloses a low level laser therapy apparatus for treatment of various tissue injuries including a handheld laser probe coupled to a control unit for selecting and controlling laser energy dosage from about 1 joule/point to about 10 joules/point. The apparatus emits laser energy at a wavelength from about 630 nm to about 904 nm, with a mean power output of between about 100 mW to about 500 mW. The apparatus further includes an access control mechanism to limit operability to trained personnel. The apparatus can only be used as a handheld device which means that the physician or ancillary medial staff needs to be present during the whole treatment session to hold the apparatus.

U.S. Pat. No. 5,616,140 discloses a battery operated, portable laser bandage having one or many lasers or hyper-red light emitting diodes imbedded in the bandage, which may be worn by a patient and applied to a specific treatment area. The device supplies the patient with a pre-programmed laser therapy regimen. The patient may wear the device for up to a week between visits to a physician. At the end of the prescribed treatment length or at the end of a week, batteries in the device may be changed or recharged and the physician may re-program the device for a different treatment regimen, if desired. The apparatus can only be used as a device worn by a patient and cannot be used as a handheld laser therapy apparatus.

It would be desirable to provide a laser therapy apparatus that could be used both as a handheld and as a patient worn apparatus.

SUMMARY OF THE INVENTION

The devices and methods described below provide for safe and convenient application of LLLT in a laser therapy apparatus which includes a laser head with a detachable battery section. When the laser head is attached to the battery section the apparatus assumes a shape like a flash-light or pen-light and can be used as a hand-held apparatus. When the laser head is detached from the battery section, a cord is used to operably connect the laser head to the battery section.

In one embodiment the apparatus is provided with a programmable controller, capable of selectively controlling the dosage and time for each laser head and the interval between the treatments. In one embodiment the laser head is attached to a bandage by slits that receive a narrow part of a substantially oval aperture of the bandage. The oval apertures may be provided in a rotary disk, so that the position of the laser head relative to the bandage can be adjusted. The laser head may then be placed in apertures of a bandage which receive and hold the laser head in proximity to the joint to be treated. The laser head, or several laser heads may be inserted into the aperture(s) to provide varying levels of treatment. In one embodiment the invention comprises a second bandage to be wrapped around a body part in the vicinity of the joint which may be provided with a pocket for receiving the battery section.

BRIEF DESCRIPTION OF THE DRAWINGS

FIG. 1 shows a laser therapy apparatus with the laser head attached to the battery section.

FIG. 2 shows a laser therapy apparatus with the laser heads detached from the battery section but operably connected though a cord.

FIG. 3 shows a bandage for holding a laser head to a joint to be treated and a bandage for holding the battery section.

FIG. 3A is a cross-sectional view of two straps of the bandage.

FIGS. 4 and 5 show details of an adjustable holder with a plurality of apertures for holding and receiving laser heads.

FIG. 6 is a side view of a second preferred embodiment of the laser therapy apparatus.

FIG. 6a is a front view of the second preferred embodiment of the laser therapy apparatus.

FIG. 7 shows a bandage for the knee.

FIG. 8 shows a bandage for the hand.

FIG. 9 shows a bandage for the wrist.

FIG. 10 shows a bandage for the shoulder.

DETAILED DESCRIPTION

Figure 11:
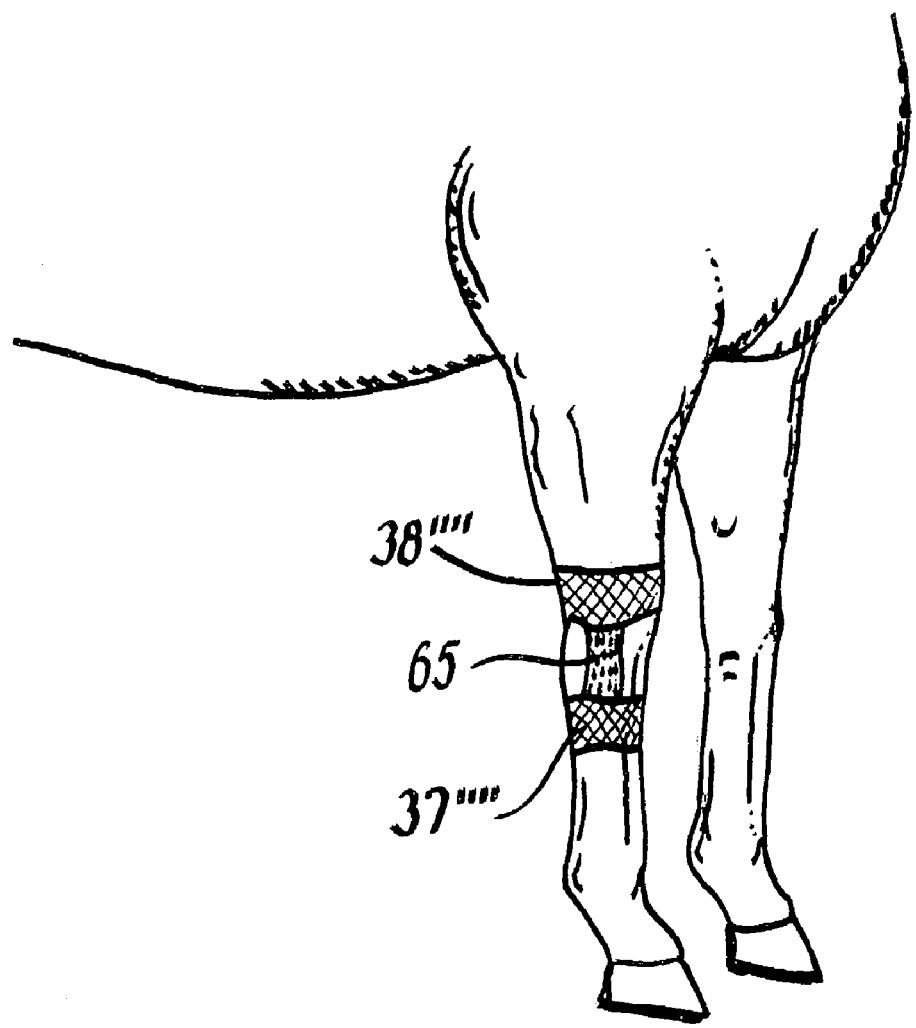
FIG. 11 shows a bandage for the knee of a horse.

FIG. 1 is a schematic illustration of a therapeutic laser apparatus 1. The laser apparatus 1 includes a laser head 10 in which a laser diode 14 is mounted. In an exemplary embodiment, a 200 (100–500) mW laser diode is mounted in head 10. The laser head 10 is 4 to 6 cm long, and has a diameter of 1.5 to 3 cm. The laser apparatus includes a battery section 12 which may be 15 to 20 cm long and a have diameter of 2 to 3 cm suitable to accommodate batteries 18. The laser head 10 and the battery section 12 are fabricated, for example, from a molded plastic material.

Electric wires connect the batteries 21 to a circuit board 23 on which the control circuitry of the programmable controller is placed. The circuit board 23 is connected to the laser diodes with two sockets 26, preferably a standard DIN socket. A button 24 for switching the laser diodes on and off is located on the battery section 12 in a position easily reached with thumb or index finger when the battery section 12 is grasped. The button 24 is connected to the circuit board 23. The laser head 10 is provided with a jack 29, that engages the socket 26 when the laser head 10 is attached to the battery section 12. The fit between the jack 29 and the socket 26 is tight enough to hold the laser head attached to the battery section 12.

As best shown in FIG. 2, spiral cords 22 are connected to the laser head 10 and to the battery section 12. Hereto, the spiral cord is provided with a jack 28, preferably a standard DIN jack, for insertion into one of the sockets 26. On its other end the spiral cord is provided with a socket 27, preferably a standard DIN socket, for receiving the jack 29 extending from the laser head 10. The cord 22 is sufficiently long to allow the laser head 10 to be moved away from the battery section 12. As shown, the battery section 12 is provided with two sockets 26, so that two laser heads 10 may be powered by one and the same battery section 12. It is also possible to provide more than two sockets 26 on the battery section 10 and connect a correspondingly higher number of laser heads 10 to the battery section.

The therapeutic laser apparatus 1 assumes the shape of a flashlight or a penlight when the laser head 10 is attached to the battery section 12. The laser diode 14 is mounted at the tip of the laser head 10 so that the laser energy beams can be projected towards a patient. The laser head 10 is provided with wiring to connect the lased diode 14 to the jack 29 for receiving electric power. The cord 22 can be detached from the laser head 10 and from the battery section 12 by unplugging the jacks from the sockets. The laser head 10 can be releasably attached to the distal end of the battery section 12 through a snap connection of the jack and socket (alternatively, a threaded wire or magnetic connection could be used). Two slits 47 are provided at diametrically opposite sides of the circumference of the laser head 10. The slits are sized and dimensioned to receive the bandage at the inner edges of the apertures. Together with the inner edge of the apertures, the slits form a means for releasably attaching the laser head to the bandage and holding the laser head relative to the aperture such that the laser diode is held over the aperture or in the aperture such that the laser diode illuminates the body under the aperture. Other means for releasably attaching the laser head, and holding the laser head over the aperture, may be uses, such as other interlocking structures such as grooves that receive the aperture borders, Velcro fasteners, snaps, etc.

When the laser head 10 is mounted on the battery section 12, the device can be used as a conventional pen- or flash light type LLLT apparatus, where the laser is held with the head in close contact with the patient's skin during treatments, typically 30 seconds to 2 minutes per treatment point.

A programmable power supply and control circuit is provided on the circuit board 23. The control circuit is capable of activating the laser heads 10 at the prescribed time and for the prescribed duration (e.g. one minute every six hours).

The laser head 10 can be attached to a bandage for hands free operation. Each joint of the body (i.e. knee, elbow, ankle, shoulder, etc.) will require a bandage, designed specifically for treatment of that joint. The bandage will generally comprise a strip of material, which may be elasticized or inelastic, provided with suitable fastening means such as Velcro® fasteners, hook and eye fasteners, or, where appropriate, the bandage may be secured to the body as a sock-like elastic tube.

FIG. 3 shows a bandage 30 suitable for use on a patient's ankle. The bandage comprises a section 37 to be wrapped around the foot distal of the ankle and a section 38 to be wrapped around just proximal of the ankle. As best shown in FIG. 3A, each section 37,38 comprises two straps 38',38" provided with a Velcro fastener for adjustably securing it about the respective body part.

The bandage 30 is provided with apertures 33 that are capable of receiving and holding laser heads 10. The apertures 33 have a substantially slightly oval inner circumference that fits to corresponding slits 47 on diametrically opposite sides of the circumference of the otherwise circular laser head 10. The laser head 10 is rotated after insertion into the aperture 33 until the narrowest part of the aperture 33 engages with the slits 47 and the laser head 10 is securely locked. The apertures do not need to be oval, they may e.g. be circular with two diametrically opposite flattened sides.

The bandage 30 may comprise a plurality of substantially oval apertures to treat different parts of the joint, e.g. for the treatment of achilles tenditis, the bandage would have a number of apertures lateral and medial for the achilles tendon.

Preferably, the apertures are provided on a holder shown best in FIGS. 4 and 5, comprising an outer ring 44 that is fixed to the bandage 30 and a disk 46 rotatably received in a groove 43 on the inner surface of the ring 44. The rotary disk 46 comprises a plurality of apertures 33 and is preferably provided with arresting positions or other means preventing it from inadvertently rotating. By rotating the disk the placement of the laser head or heads can be adjusted.

In operation, the bandage 30 is affixed to the joint to be treated by the patient, a physician, or ancillary medical staff, using the straps 37,38 such that the bandage 30 is properly positioned. The straps may be made of a stretchable material to allow the bandage to be strapped around the patient's body parts and to apply a positive biasing force to hold the bandage in place on the joint to be treated.

FIG. 3 shows a second bandage 60 provided with a pocket 62 for receiving and holding the battery section 12. The second bandage 60 comprises two straps provided with a Velcro fastener. The second bandage 60 is tightly wrapped around the upper leg of the patient. The cord 22 extends along the patient's leg, and the complete system can be hidden under a normal pair of pants. The laser heads located in the first bandage on the ankle can be operated with a switch located on the battery section 12 which is held in the pocket in the second bandage.

The programmable controller is preferably provided with an infrared communications port 55, preferably of the IrDA standard capable of communication with a corresponding port of a computer such as the PC of the physician. Alternatively the programmable controller may be provided with an RF receiver in accordance with the Bluetooth standard, or a cable connector for more conventional communication with a PC via a cable. The physician enters the treatment regime into the PC and sends it via the IrDA port to the laser apparatus 1.

After being placed on the joint to be treated, the patient simply wears the device for the prescribed period of time and is free to conduct themselves in the normal course. The device automatically delivers the prescribed low level laser therapy as determined by the programmable controller while the patient goes about their normal routine.

FIGS. 6 and 6a shows another preferred embodiment of the invention in that comprises a larger battery section 12'. The battery section is shown as a flat type, but any other shape could be used. The exemplary battery section is provided with three sockets 26 for receiving the jacks 29 of up to a corresponding number of laser heads 10. The laser therapy apparatus according to this embodiment can be used as a handheld device to treat a larger area of a joint with a plurality of laser heads activated simultaneously. The laser apparatus according to this embodiment can also be used with a plurality of laser heads, in this example up to three, attached to a bandage and connected to the battery pack via cords 22. The larger battery pack may in this case be attached to the body by a dedicated bandage 60'.

FIG. 7 shows a bandage 30' for use with the knee. The bandage comprises a section 37' to be wrapped around just under the knee, and a section 38' to be wrapped around just above the knee, to support a laser mounting structure 60 which includes numerous apertures 33 for holding laser diodes or heads sized and dimensioned to fit securely in the apertures. The bandage 60' for carrying the battery pack is wrapped around the proximal segment of the thigh. Similarly, the lower section of the bandage can be sized for use on the elbow, to be wrapped around the forearm just under the elbow, and an upper section can be wrapped around the arm just above the elbow, and the bandage for carrying the battery pack is wrapped around upper arm, to enable application of the laser therapy to the elbow of the patient.

FIG. 8 shows a bandage 30" for use with the hand or wrist. The bandage comprises a section 37" to be wrapped around hand, and a section 38" to be wrapped around the pad. The bandage for carrying the battery pack is wrapped around upper arm. FIG. 9 shows the bandage adapted for application of the laser diodes over the palmar side of the wrist, in an area overlying the carpal tunnel (for the treatment of carpal tunnel syndrome). In both FIGS. 8 and 9, the bandage includes the laser mounting structures 61 which includes numerous apertures 33 for holding laser diodes or heads sized and dimensioned to fit securely in the apertures over the target area of the hand or wrist.

FIG. 10 shows a bandage 30''' for use with the shoulder. The bandage comprises a section 37''' to be wrapped around the upper part of the truncus and a part 38''' perpendicular to this and connecting the front and back part of the band. The holder with slits is located to cover the insertions of the biceps tendons. The bandage 60' for carrying the battery pack is wrapped around upper arm.

FIG. 11 shows a bandage 30'''' that is particularly suitable for treatment of the knee of a horse. The bandage comprises as section 37'''' that is wrapped around just distal of the joint and a section 38'''' that is wrapped around proximal of the joint. The bandage comprises a holder with a plurality of apertures 33 for receiving and holding laser heads 10. The bandage 60' for carrying the battery pack is wrapped around the proximal segment of the thigh.

According to another preferred embodiment (not shown) the laser heads 10 are provided with a switch that deactivates the laser head when is detached from the holder (this switch is overruled when the laser head is attached to the battery section 12). This safety feature is preferably obtained by letting the apertures 33 be part of an electrical circuit that powers the laser 14, e.g. by providing an electrically conductive inner circumference of the apertures 33 in combination with an electrode in each of the slits 47 or providing contact relays or contact sensors within the slits. Thus the electrical circuit is closed only when the laser head 10 is placed in the aperture 33 with the contacts in the slits 47 engaging the electrically conductive inner circumference of the aperture 33. With this arrangement the power supply will be cut off if one of the laser heads 10 is detached from the bandage. Thus, the lasers 14 will stop emitting the moment they are not connected to the bandage, which is important because the laser light can damage the eye. Furthermore the Velcro fastener can be part of the electrical circuit, so in the moment the fastener is opened, the circuit is broken.

In use, the controller may be programmed through the communications port 55 to provide laser output on a predetermined schedule, for predetermined treatment periods.

The laser head or heads may be placed in selected apertures of the bandage chosen according to the desired treatment site. Thereafter, the patient may carry on as desired while the desired therapy is applied without the need for constant attention by an operator. A clear advantage of the present system for providing low level laser therapy is the reduced time required by a medical staff to apply the laser, and the possibility to use the laser as a handheld device as well. Thus, a physician may diagnose a patient with a malady such as carpal tunnel syndrome, decide upon a course of treatment of periodic applications of low level laser energy to the carpal tunnel area of the wrist, and program this treatment program in to the device, and the patient may thereafter apply the device to the wrist so that treatment is automatically applied. Thus, the therapy can be applied without immediate supervision of a therapist, enabling chronic or long term treatment at much lower cost than has been previously available.

Although the present invention has been described in detail for purpose of illustration, it is understood that such detail is solely for that purpose, and variations can be made therein by those skilled in the art without departing from the scope of the invention. Thus, while the preferred embodiments of the devices and methods have been described in reference to the environment in which they were developed, they are merely illustrative of the principles of the inventions. Other embodiments and configurations may be devised without departing from the scope of the appended claims.

The invention claimed is:

1. A method for applying Low Level Laser Therapy comprising:
    providing a laser head section comprising a laser diode, said laser head section couplable to a distensible cord or directly to a battery section;
    providing the battery section, said battery section capable of powering the laser diode and further comprising a programmable controller capable of selectively controlling the dosage and time of treatment for the laser head section;
    providing a first bandage comprising a coupling means for coupling the laser head to the first bandage;
    providing a second bandage comprising a coupling means for coupling the battery section to the second bandage;
    providing the distensible cord couplable to the battery section and the laser head section;
    coupling the laser head to the first bandage;
    coupling the battery section to the second bandage;
    coupling the cord to the batter section and the laser head section;
    coupling the first bandage and second bandage to a patient's body; and
    delivering optical radiation to a portion of the patient's body from the laser head section.

* * * * *